US00PP27258P3

(12) United States Plant Patent
Helvick et al.

(10) Patent No.: US PP27,258 P3
(45) Date of Patent: Oct. 11, 2016

(54) ***GARDENIA* PLANT NAMED 'PIIGA-II'**

(50) Latin Name: ***Gardenia jasminoides* L.**
Varietal Denomination: PIIGA-II

(71) Applicant: Plant Introductions, Inc., Watkinsville, GA (US)

(72) Inventors: Rhonda Helvick, Madison, GA (US); Oren McBee, Bishop, GA (US); Mark Griffith, Watkinsville, GA (US); Jeff Beasley, Lavonia, GA (US); Michael A. Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 181 days.

(21) Appl. No.: 14/121,509

(22) Filed: Sep. 12, 2014

(65) Prior Publication Data

US 2016/0081249 P1 Mar. 17, 2016

(51) Int. Cl.
*A01H 5/02* (2006.01)

(52) U.S. Cl.
USPC ..... Plt./255

(58) Field of Classification Search
USPC ..... Plt./255
See application file for complete search history.

*Primary Examiner* — Keith Robinson
(74) *Attorney, Agent, or Firm* — Lathrop & Gage LLP

(57) ABSTRACT

A new and distinct cultivar of *Gardenia jasminoides* plant named 'PIIGA-II', characterized by fragrant, double white flowers, abundant large flowers in spring with reblooming to fall, lustrous, dark green foliage, compact upright growth habit, and cold hardy to USDA Hardiness Zone 7.

3 Drawing Sheets

Genus and species of plant claimed: *Gardenia jasminoides* L.

Variety denomination: 'PIIGA-II'.

BACKGROUND OF THE INVENTION

The present invention relates to a new and distinct cultivar of *Gardenia jasminoides* 'Double Mint'×'PIIGA-I', a member of the Rubiaceae family, hereinafter referred to by its cultivar name 'PIIGA-II'. This cultivar is grown primarily as an ornamental for landscape use and for use as a potted plant.

The new *Gardenia* cultivar originated from a controlled pollination seed of of *Gardenia jasminoides* 'Double Mint' (U.S. Plant Pat. No. 23,507)×'PIIGA-I' (U.S. Plant Pat. No. 22,510) as part of a planned breeding program to develop reblooming, double-flowered, cold hardy *gardenias*. The cultivar 'PIIGA-II' originated in 2012 and was selected in a cultivated environment in Watkinsville, Ga. from the progeny of this cross-pollination by continued evaluation for growth habit and foliage and flower characteristics.

'PIIGA-II' has been asexually reproduced by softwood cuttings in Watkinsville, Ga. since 2013, and the characteristics of the cultivar have been stable and reproduced true-to-type in successive vegetative generations.

SUMMARY OF THE INVENTION

'PIIGA-II' has not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'PIIGA-II' from all other varieties in commerce known to the inventor. 1) Fragrant, double white flowers. 2) Abundant large flowers in spring with reblooming to fall. 3) Lustrous, dark green foliage. 4) Compact upright growth habit. 5) Cold hardy to USDA Hardiness Zone 7. There are no other cultivars of *Gardenia* with this combination of characteristics known to the inventor.

'PIIGA-II' is distinguished from its female parent, '*Gardenia jasminoides* ' 'Double Mint' (U.S. Plant Pat. No. 23,507), by its growth habit, foliage size, flower size, and amount of re-bloom. 'PIIGA-II' has a larger, more upright growth habit than 'Double Mint'. 'PIIGA-II' has larger foliage than 'Double Mint'. 'PIIGA-II' has a larger flower than 'Double Mint' with more reblooming.

'PIIGA-II' is distinguished from its male parent 'PIIGA-I' (U.S. Plant Pat. No. 22,510), by its flowers, growth habit, and rebloom. 'PIIGA-II' has large double flowers, upright growth habit, and abundant rebloom in the fall; whereas 'PIIGA-I' has single large flowers, compact rounded growth habit, and rarely reblooms.

'PIIGA-II' can be compared to 'Crown Jewel' (U.S. Plant Pat. No. 19,896), but differs in the following characteristics. 'PIIGA-II' has upright growth habit, whereas 'Crown Jewel' has a spreading growth habit. 'PIIGA-II' has larger foliage than 'Crown Jewel'. 'PIIGA-II' re-blooms from spring to fall, whereas 'Crown Jewel' only flowers in spring. 'PIIGA-II' is more resistant to root rot in production than 'Crown Jewel'.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Gardenia*.

DETAILED DESCRIPTION

Figure 1:
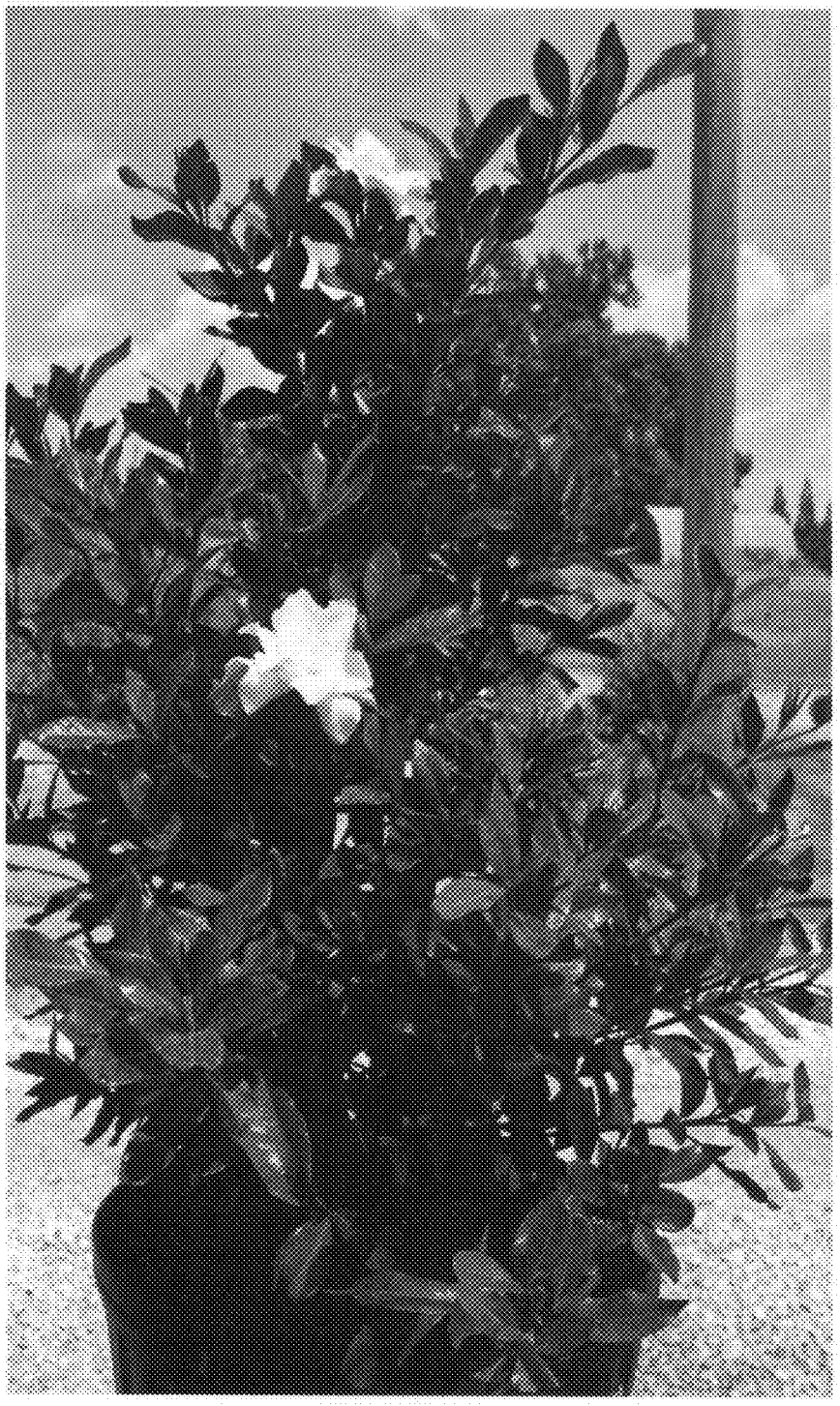
FIG. 1 shows the overall appearance of a two-year-old plant of 'PIIGA-II' in a container.
Figure 2:
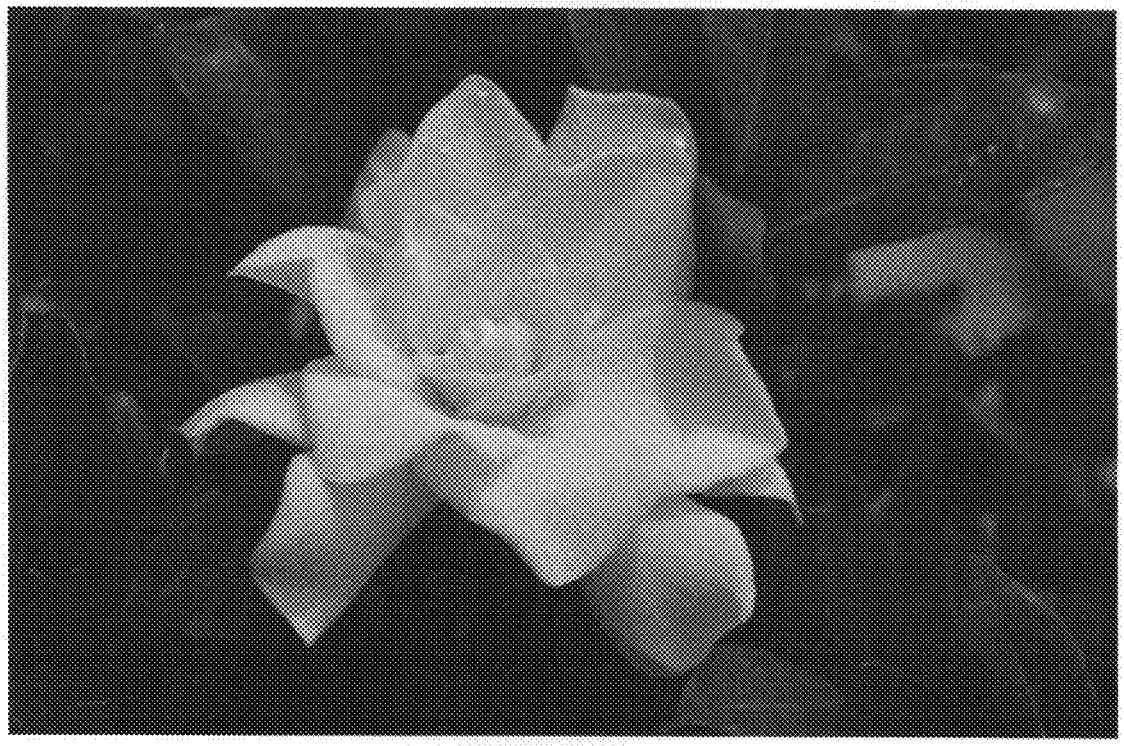
FIG. 2 shows a close-up view of a flower of a two-year-old 'PIIGA-II' plant.
Figure 3:
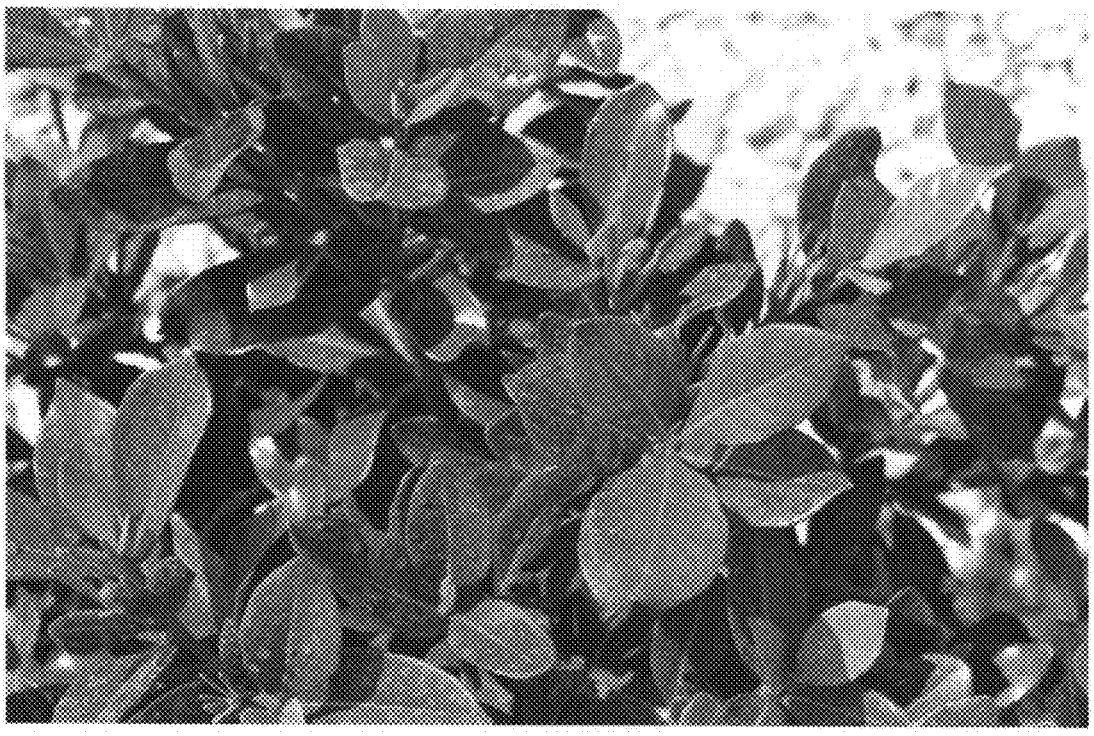
FIG. 3 shows a close up photo of the foliage of a two-year-old 'PIIGA-II' plant.

In the following description, color references are made to The Royal Horticultural Society Colour Chart, 2007 Edition, except where general terms of ordinary dictionary significance are used. Plants used for the description were approximately 2 years old and were grown in 11.8 L containers in full sun under outdoor conditions in Watkinsville, Ga.

Botanical classification: *Gardenia* hybrid cultivar 'PIIGA-II'.

Parentage:

*Female, or seed parent.*—*Gardenia jasminoides* 'Double Mint' (U.S. Plant Pat. No. 23,507).

*Male, or pollen parent.*—*Gardenia jasminoides* 'PIIGA-I' (U.S. Plant Pat. No. 22,510) (controlled-pollination).

Propagation: Terminal cuttings.

Time to initiate roots, summer: About 21 days at 32° C.

Time to produce a rooted young plant, summer: About 4 months at 32° C.

Plant description: The claimed variety is a freely branching, upright, evergreen shrub. The plant is hardy in USDA Zones 7 to 9.

*Propagation.*—Stem cuttings.

*Time to initiate roots in summer.*—About 21 days.

*Root description.*—Numerous, fibrous, and well-branched.

*Plant size.*—About 60 cm high from the soil level to the top of the foliage and about 51 cm wide after about 3 years.

*First year stems.*—Having a diameter of about 3 mm. Length: about 20 cm. Shape: round. Pubescence: finely hairy.

*First year stem color* (*young*).—143C. Color (woody): 200A.

*Stem strength.*—Flexible when young, more easily broken once mature.

*Internode length.*—About 3 cm.

*Second year and older stems.*—Have a diameter of about 5 mm or more. Length: about 43 cm. Internode length: 3 cm. Strength: Stems easily broken once they are mature. Shape: round. Pubescence: none, lose all pubescence by $2^{nd}$ year.

*Second year and older stem color.*—200A.

*Bark.*—Some stringy exfoliation beginning on second year stems.

*Trunk diameter.*—About 1.7 cm at the soil line.

*Color.*—N200A.

Vegetative bud description:

*Vegetative buds.*—Arrangement: opposite. Shape: conical, single-scaled. Size: about 3 mm in length, about 1 mm in width; Color: 144C.

Foliage description:

*Arrangement.*—Opposite some whorled, especially at the terminal end of the shoot.

*Length.*—About 6 cm.

*Width.*—About 2 cm.

*Shape.*—Lanceolate.

*Apex.*—Acuminate.

*Base.*—Cuneate.

*Margin.*—Entire.

*Texture* (*upper and lower surfaces*).—Glabrous, lustrous, no pubescence.

*Venation.*—Pinnate.

*Venation color* (*upper and lower surfaces*).—145A.

*Color of emerging foliage.*—144A on the upper surface, and 144C on the lower surface.

*Color of mature foliage.*—N137A on the upper surface, and 146A on the lower surface.

*Petiole length.*—About 2 mm.

*Petiole diameter.*—About 3 mm.

*Petiole texture.*—Glabrous.

*Petiole color* (*upper and lower surfaces*).—146A.

Flower description:

*Flower type and habit.*—Flowers are borne singly at the terminals and in the axils where two stems divide. Individual flowers are showy for about 2 days and remain on the plant for about 1 to 2 weeks after they have senesced.

*Bloom period.*—Spring to frost. Flowers are produced abundantly from May to June, and then sporadically through November in Watkinsville, Ga.

*Fragrance.*—Exceedingly sweet fragrance.

*Flower diameter.*—About 7 cm.

*Height or depth.*—About 4 cm.

*Flower bud diameter.*—About 1 cm.

*Flower bud length.*—About 4.5 cm.

*Flower bud shape.*—Oblong.

*Flower bud color.*—143A.

*Calyx.*—About 4 cm in length, about 1.5 cm in width, and 143A in color.

*Sepals.*—Arrangement/quantity: star shaped calyx with five sepals fused at the base. Length: about 4.5 cm. Width: about 4 mm. Shape: lanceolate. Apex: acute. Margin: entire. Texture on upper and lower surface: smooth, glabrous. Color on upper and lower surface: 143C.

*Peduncles*.—Length: about 1 cm. Diameter: about 4 mm. Angle: upright. Strength: strong. Texture: Smooth, glabrous. Color: 143A.

*Pedicels.*—About 2 cm in length, 7 mm in diameter, glabrous, and 144A in color.

Petals:

*Quantity.*—6 to 8 true petals and 16 to 18 petaloids per flower.

*True petal.*—Length: About 2.4 cm. Width: about 2.3 cm. Shape: obovate, Apex: rounded. Base: Attenuate. Margins: entire, with undulating margins and overlapping in arrangement to form a whorl. Texture: thick, glabrous on upper and lower surface. Color: at peak bloom the upper and lower surfaces are 155C aging to 11C and eventually to N199D before dehiscing.

*Petaloid.*—Length: Ranges from 1.5 to 2.5 cm, becoming smaller toward the top and center of the flower. Width: ranges from 1.1 to 2.1 cm, becoming smaller toward the top and center of the flower. Shape: Texture: thick, glabrous on upper and lower surface. Color: at peak bloom the upper and lower surfaces are 155C aging to 11C and eventually to N199D before dehiscing.

Stamens:

*Quantity.*—4 to 6 per flower, sometimes petaloid or malformed. There is no separate filament structure present, instead the anthers are fused to the base of the petals.

*Anthers.*—About 8 mm long and about 2 mm wide.

*Shape.*—Lanceolate.

*Color.*—199A. Pollen: either nonexistent or produced in small quantities and color is 8B.

Pistils:

*Quantity/arrangement.*—One per flower, inferior.

*Pistil length.*—About 1.8 cm.

*Pistil diameter.*—About 4 mm.

*Stigma shape.*—Obovate, about 7 mm length and about 4 mm in diameter.

*Stigma color.*—1C. Style: color is 154D, about 3 cm in length, and about 1.5 mm in width.

*Ovary.*—Color is 2C, about 5 mm in length, about 4 mm in width, elliptoid in shape, and contains many (50 or more) very small (less than 1 mm) ovules.

Fruit: No fruit set observed.

Disease/pest resistance: No specific pest or disease resistance or susceptibility has been observed.

I claim:

1. A new and distinct *Gardenia jasminoides* plant named 'PIIGA-II', substantially as illustrated and described herein.

* * * * *